United States Patent [19]

Osypka

[11] Patent Number: 4,687,469
[45] Date of Patent: Aug. 18, 1987

[54] DEVICE FOR SLITTING INTRODUCERS FOR PACEMAKER ELECTRODES

[76] Inventor: Peter Osypka, Basler Strasse 109, D-7889 Grenzach-Wyhlen, Fed. Rep. of Germany

[21] Appl. No.: 740,013

[22] Filed: May 31, 1985

[30] Foreign Application Priority Data

Jun. 1, 1984 [DE] Fed. Rep. of Germany ....... 3420455

[51] Int. Cl.$^4$ ............................................ A61M 25/00
[52] U.S. Cl. ................................. 604/161; 128/419 P; 128/784
[58] Field of Search ..................... 128/419 P, 642, 754, 128/784, 786; 604/158, 160–161, 164, 280, 165–166; 30/90.1, 90.4

[56] References Cited

U.S. PATENT DOCUMENTS

| 3,190,290 | 6/1965 | Alley et al. | 604/280 |
|---|---|---|---|
| 3,454,006 | 7/1969 | Langdon | 604/164 |
| 3,624,901 | 12/1971 | Pettit et al. | 30/90.4 |
| 3,898,733 | 8/1973 | Cormier | 30/90.4 |
| 3,902,501 | 9/1975 | Citron et al. | 128/785 |
| 4,166,469 | 9/1979 | Littleford | 128/419 P |
| 4,243,050 | 1/1981 | Littleford | 128/419 P |
| 4,345,606 | 8/1982 | Littleford | 128/419 P |
| 4,354,491 | 10/1982 | Marbry | 604/161 |
| 4,402,685 | 9/1983 | Bühler et al. | 604/280 |
| 4,412,832 | 11/1983 | Kling et al. | 604/280 |
| 4,473,067 | 9/1984 | Schiff | 128/1 D |
| 4,565,545 | 1/1986 | Suzuki | 604/164 |

Primary Examiner—William E. Kamm
Attorney, Agent, or Firm—Peter K. Kontler

[57] ABSTRACT

Apparatus for implanting pacemaker electrodes whose proximal ends have enlarged plugs for attachment to pacemakers has a one-piece unslotted and unweakened tubular introducer of somewhat flexible material whose front end portion is inserted into the subclavian vein of the patient with assistance from a guide wire and a dilator. The dilator and the guide wire are thereupon extracted from the introducer so that the latter provides an unobstructed passage for implantation of a pacemaker electrode. The exposed section of the implanted electrode between the rear end of the introducer and the plug is then engaged by the trough-shaped elastically deformable portion of a severing device whose knife extends radially of the exposed section of the electrode and severs the introducer longitudinally while the latter is being pulled in a direction to extract its front end portion from the vein. The rear end of the introducer is formed with wing-shaped handgrip portions which facilitate the pulling of introducer in a direction toward the cutting edge of the knife and the exertion of a simultaneous lateral pull upon the rear end of the introducer so that the latter is automatically separated from the exposed section of the electrode simultaneously with longitudinal slitting by the cutting edge.

10 Claims, 13 Drawing Figures

DEVICE FOR SLITTING INTRODUCERS FOR PACEMAKER ELECTRODES

BACKGROUND OF THE INVENTION

The present invention relates to improvements in apparatus for implanting pacemaker electrodes, catheters and similar slender elongated objects into the circulatory systems or cavities of animal bodies, especially human patients.

The article "Permanente Herzschrittmacherversorgung mittels perkutaner Implantationstechnik" on pages 489–494 of the German-language publication entitled "Herz/Kreislauf 10" (Nov. 10, 1978) describes an apparatus which employs a syringe with a hollow metallic needle serving for introduction of a guide wire into a selected vein (e.g., into the subclavian vein) so that the guide wire can facilitate the insertion of a plastic sleeve- or hose-like introducer with assistance from a rigid dilator. Once a portion of the introducer is properly inserted into the vein, the guide wire and the dilator are extracted so that the introducer provides an unobstructed passage for implantation of a pacemaker electrode, a catheter or a similar elongated object which is to be permanently or temporarily implanted in the body. In a final step, the introducer is severed longitudinally so as to permit its separation from the implanted object. The guide wire is normally a so-called Seldinger spiral which is caused to pass through the hollow needle of the syringe as soon as the tip of the needle has penetrated into the selected vein and as soon as the cylinder and piston of the syringe are detached from the needle. The convolutions of the Seldinger wire allow for convenient introduction of the front end portion of the introducer and of the hollow cylindrical dilator therein into the vein by rotating the dilator and the introducer around the wire. The guide wire and the dilator are thereupon withdrawn from the vein and from the introducer while the corresponding part of the body is monitored by an X-ray machine.

Extraction of the introducer upon completed implantation of a pacemaker electrode and its separation from the implanted object present problems because the exposed proximal end of the implanted pacemaker electrode carries a plug by means of which the electrode is connectable to a pacemaker. The dimensions of the plug (as measured radially of the electrode) exceed the inner diameter of the introducer so that the latter cannot be slipped over the plug. Consequently, the introducer must be severed longitudinally and/or otherwise in order to allow for its separation from the implanted electrode without the need to remove the plug or to attach the plug to the electrode upon completed implantation into the body of the patient. The aforementioned German-language publication offers two solutions, namely to separate the plug from the implanted electrode or to use shears or a similar cutting implement in order to slit the introducer longitudinally so as to allow for its separation by moving it radially of and away from the exposed section of the implanted electrode.

U.S. Pat. Nos. 4,243,050 and 4,345,606 to Littleford propose to employ a tubular introducer which is formed with a longitudinally extending slot prior to putting it to actual use. This reduces the problem of separating the introducer from the exposed section of the implanted electrode without removing the plug but such types of preslotted sleeve-like introducers present many other equally serious or even graver problems. Thus, the introducer should exhibit at least some flexibility so that it can conform to the anatomy of a patient in the region where a portion thereof is introduced into the body for the purpose of establishing a path for implantation of a pacemaker electrode or the like. The longitudinally extending slot weakens the introducer so that the latter is likely to exhibit excessive flexibility and to actually buckle prior to or during implantation of an electrode or the like. This necessitates extraction of the introducer and restarting of the entire procedure, i.e., puncturing of the vein with the needle of a syringe, insertion of a guide wire, insertion of an introducer and a dilator, and extraction of the dilator and guide wire upon completed insertion of the front end portion of the introducer into the vein. On the other hand, if the preslotted introducer is relatively stiff so that it cannot undergo excessive flexing in spite of the longitudinally extending slot therein, the material of the introducer is likely to damage the relatively soft layer of insulating material which surrounds the pacemaker electrode. In other words, the rigidity of the introducer cannot be increased at will because an excessively rigid introducer is not likely to assume an optimum shape for implantation of an electrode or the like, and such rigid introducer is likely to damage the implanted object as a result of contact between the edges bounding its slit and the insulating material on the electrode.

U.S. Pat. No. 4,243,050 to Littleford also discloses an introducer having two slotted tubes which are partially telescoped into each other. When the inner tube is completely withdrawn from the outer tube, each of these tubes can be readily separated from the exposed section of a pacemaker electrode because its longitudinally extending slot has or can have a width at least matching the diameter of the electrode. The just discussed proposal exhibits the drawback that the introducer is quite expensive and complex as well as that a lengthy manipulation is necessary to separate its components from the implanted object. Furthermore, the electrode cannot be reliably held while the inner tube of the two-piece introducer is fully extracted from the outer tube as well as that large quantities of body fluid can escape by way of the introducer during separation of its components from the exposed section of the electrode. Moreover, if the slot in the one and/or the other component of such composite introducer is too narrow, the person in charge must use shears, a scalpel or another severing implement to separate the respective component from the implanted object. The shears and scalpel are likely to damage the insulation on the implanted electrode.

German Offenlegungsschrift No. 23 43 094 of Nordström discloses an introducer with two longitudinally extending weakened portions which allow for separation of a longitudinally extending strip therebetween. Such introducers are expensive and their flexibility cannot be controlled with a requisite degree of accuracy.

German Gebrauchsmuster No. 71 03 368 of Braun discloses an apparatus for implantation of a flexible catheter which also employs an introducer with two longitudinally extending weakened portions.

German Gebrauchsmuster No. 79 28 830 of Technological Supply, S. A. discloses an introducer which is slotted all the way from end to end prior to actual use.

OBJECTS AND SUMMARY OF THE INVENTION

An object of the invention is to provide novel and improved means for facilitating separation of an introducer, which is devoid of a longitudinally extending slot and/or of one or more longitudinally extending weakened portions, from the exposed section of an implanted object.

Another object of the invention is to provide a novel and improved introducer severing device for use in the above outlined apparatus.

The invention provides a severing device for use with an apparatus for introducing an elongated slender object into an animal body, particularly for introducing a pacemaker electrode or a catheter into a vein of a patient. The apparatus comprises a severable tubular introducer (preferably in the form of a reasonably rigid but still flexible sleeve made of a suitable synthetic plastic material) the first end portion of which can be caused to extend into the body in a conventional manner, e.g., by employing a syringe, a wire guide and a dilator and by thereupon withdrawing the dilator and the wire guide. The second end portion of the introducer is located outside of the body which receives the first end portion so that an elongated slender object can be inserted or implanted into the body by way of the second end portion, thereupon by way of a series of intermediate portions and ultimately by way of the first end portion of the introducer until a first section of the thus inserted object extends beyond the first end portion (e.g., all the way into the heart of a patient who is to receive a pacemaker) and a second section of the inserted object extends outwardly beyond the second end portion of the introducer. The improved severing device for the introducer comprises a supporting portion which can be caused to releasably engage the second section of the inserted object and a knife which is provided on the supporting portion and has at least one cutting edge facing the second end portion of the introducer when the supporting portion engages the second section of the inserted object so that the introducer is automatically severed longitudinally in response to its movement in a direction to extract the first end portion from the body and to advance the second end portion, successive intermediate portions and ultimately the first end portion of the introducer toward and against the cutting edge or cutting edges.

The supporting portion of the severing device is preferably elongated for more convenient manipulation and application to the second section of the inserted object and extends beyond the knife in at least one direction as considered longitudinally of the second section of the inserted object. Such supporting portion can be formed with a longitudinally extending slot so that it can be placed around the second section of the inserted object; to this end, the supporting portion is preferably a substantially trough-shaped part having a C-shaped or U-shaped cross-sectional outline. The supporting portion is preferably deformable so that it can be moved into desired frictional engagement with the second section of the inserted object. To accomplish this object, the supporting portion consists (at least in part) of a suitable elastomeric material. Furthermore, the supporting portion can be configurated so as to conform to one or more fingers of the hand which is used to hold the supporting portion in engagement with the second section of the implanted object. For example, the supporting portion can be formed with one or more flutes or analogous recesses. The knife of the severing device is preferably located between the second end portion of the introducer and the flute or flutes of the supporting portion when the latter engages the second section of the inserted object.

The supporting portion of the severing device preferably further comprises a terminal which is receivable in the second end portion of the introducer to at least partially stem the outflow of body fluids (particularly blood from a vein) by way of the introducer while the first portion of the introducer extends into the body. Such terminal can constitute a substantially conical tip which is preferably adjacent to the cutting edge of the knife.

The second end portion of the introducer is preferably provided with at least one substantially wing-like handgrip portion which can be grasped by fingers to pull the second end portion in a direction toward the cutting edge to thereby extract the first end portion from the body and to simultaneously split the introducer longitudinally in a direction from the second toward the first end portion. In accordance with a presently preferred embodiment, the second end portion of the introducer has a plurality of handgrip portions, most preferably two handgrip portions which are normally located substantially diametrically opposite each other and extend radially outwardly from the second end portion. At least one of such plurality of handgrip portions is preferably movable relative to the other handgrip portion(s) into close or immediate proximity of another handgrip portion to form therewith a relatively large handle which can be engaged by the fingers of a person preparatory to and during pulling of the second end portion in a direction to extract the first end portion from the body. The handgrip portions are preferably integral parts of the introducer. At least one of the handgrip portions can be provided with at least one flute or an analogous recess for reception of a portion of a finger of the hand which is used to move the movable handgrip portion relative to another handgrip portion. The handgrip portions which form the aforementioned handle preferably have substantially flat abutting edge faces.

The novel features which are considered as characteristic of the invention are set forth in particular in the appended claims. The improved severing device itself, however, both as to its construction and the mode of utilizing the same, together with additional features and advantages thereof, will be best understood upon perusal of the following detailed description of certain specific embodiments with reference to the accompanying drawing.

DESCRIPTION OF THE PREFERRED EMBODIMENTS

Figure 1:
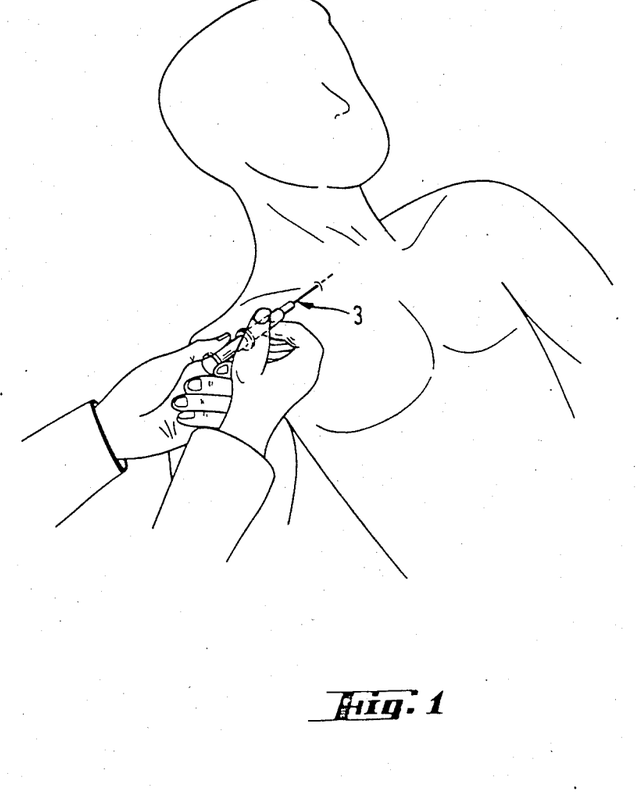
FIG. 1 is a perspective view of a syringe whose hollow needle is in the process of being inserted into the subclavian vein of a patient.
Figure 2:
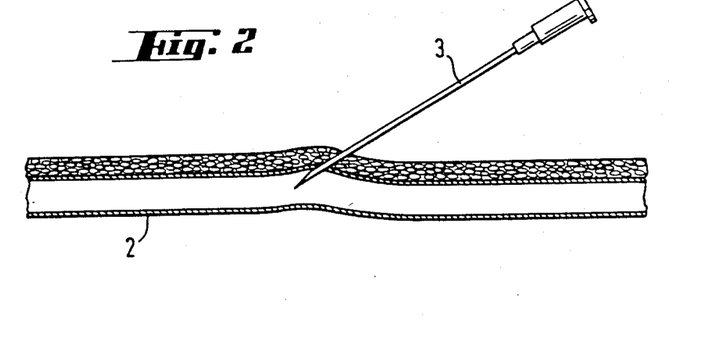
FIG. 2 is an enlarged elevational view of the needle and a sectional view of the vein, showing the tip of the needle in the vein.
Figure 3:
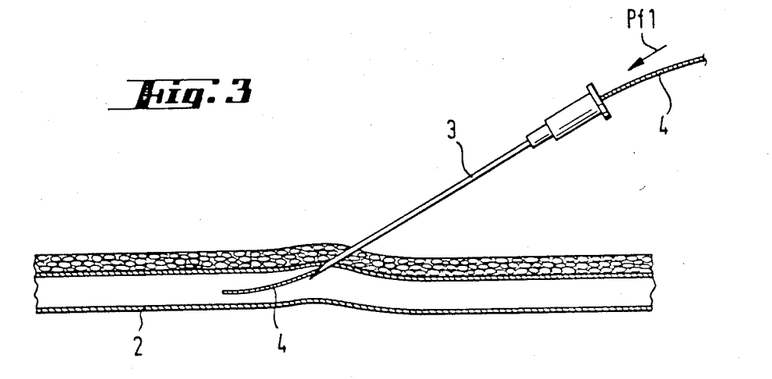
FIG. 3 illustrates the structure of FIG. 2 and a portion of a guide wire which extends through and beyond both ends of the needle.
Figure 4:
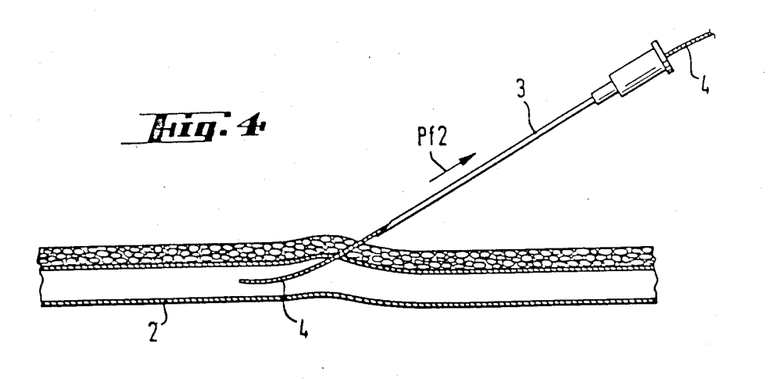
FIG. 4 illustrates the structure of FIG. 3, with the needle shown in a position immediately upon extraction of its tip from the vein.

FIG. 1 shows a syringe with a hollow metallic needle 3 which is in the process of being inserted into the subclavian vein 2 (see FIG. 2) of a patient. The purpose of the needle 3 is to facilitate implantation of a pacemaker electrode 1 (see FIG. 7), a catheter or another elongated slender object into the circulatory system, especially into the heart, of the patient. The needle 3 punctures the vein 2 in a manner as shown in FIG. 2 (so that its tip extends into the vein) and is then detached from the remainder of the syringe so that its rear end portion is accessible for insertion of an elongated flexible guide wire 4 in the direction indicated by the arrow Pf1 (see FIG. 3). The needle 3 and the guide wire 4 constitute two conventional constituents of the apparatus which is used to implant the electrode 1 into the body of the patient. The guide wire 4 can constitute a so-called Seldinger spiral which can be flexed (see FIG. 3) so that its front end portion can penetrate into the vein 2 beyond the tip of the needle 3. In the next step, the needle 3 is extracted from the body of the patient in the direction of arrow Pf2 (see FIG. 4) by sliding toward and beyond the exposed end portion of the guide wire 4 while the front end portion of the guide wire remains in the vein 2.

Figure 5:
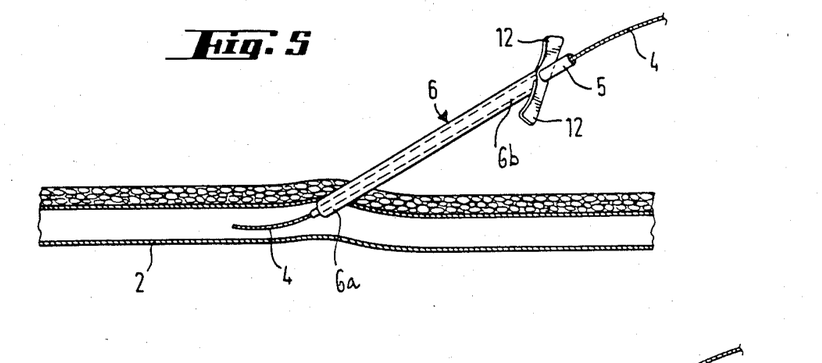
FIG. 5 shows the vein and the guide wire of FIG. 4 as well as a sleeve-like introducer whose first end portion is already introduced into the vein and which confines the major portion of a cylindrical dilator while the latter surrounds the guide wire.
Figure 6:
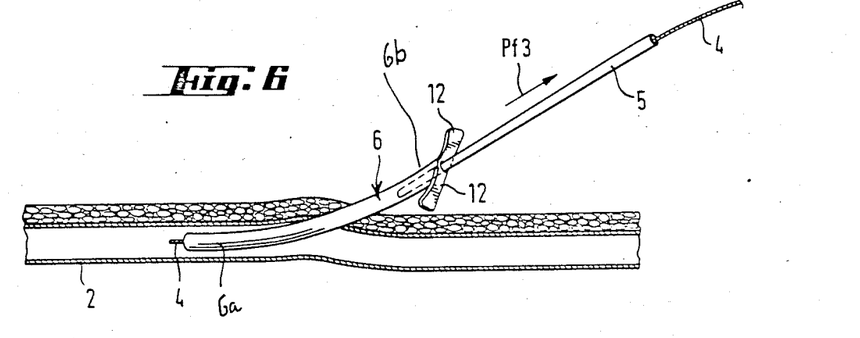
FIG. 6 shows the structure of FIG. 5 with the dilator and guide wire in the process of being extracted from the introducer.
Figure 7:
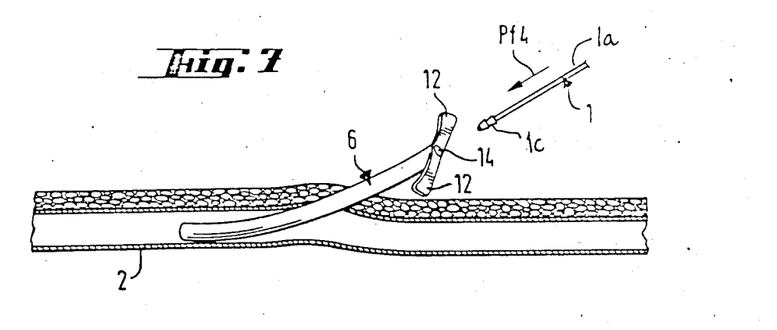
FIG. 7 illustrates the vein and the introducer of FIG. 6 and the leading end of a pacemaker electrode which is about to enter the exposed second end portion of the introducer.
Figure 8:
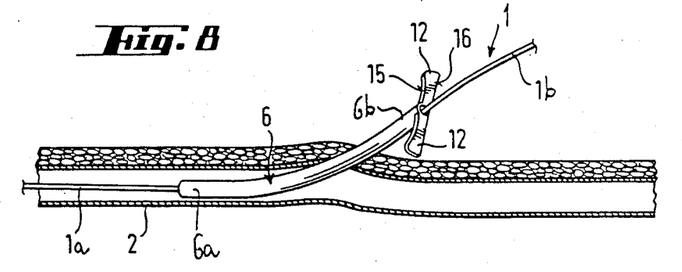
FIG. 8 shows the structure of FIG. 7, with the electrode fully inserted.

The apparatus further comprises a relatively rigid but flexible sleeve-like introducer 6 which is preferably made of a suitable synthetic plastic material, and an elongated rigid hollow cylindrical dilator 5 which can be inserted into the introducer 6 so that its front end portion extends beyond the first or front end portion 6a of the introducer 6 and that its rear end portion extends beyond the second or rear end portion 6b of the introducer 6. This can be seen in FIG. 5 which shows the front end portion 6a of the introducer 6 temporarily implanted in the body of the patient, i.e., the first end portion 6a extends into the vein 2. The wire 4 serves as a reliable guide for convenient introduction of the first end portion 6a into the vein 2, and the dilator 5 stiffens the introducer 6 during such insertion so as to reduce the likelihood of extensive bending or buckling. The dilator 5 is inserted into the introducer 6 before it is slipped onto the guide wire 4 and before it is moved to the position of FIG. 5 in which the first end portion 6a of the introducer is already implanted in the body of the patient. In the next step (see FIG. 6), the guide wire 4 and the dilator 5 are extracted from the introducer 6 and the latter is pushed deeper into the vein 2 so that its first end portion 6a as well as the majority of its intermediate portions between the end portions 6a, 6b extend into and in the longitudinal direction of the channel which the vein 2 defines for the flow of body fluid therein. The direction in which the guide wire 4 and the dilator 5 are extracted from the introducer 6 is indicated by the arrow Pf3 which is shown in FIG. 6. The introducer 6 is at least slightly flexible and can flex as soon as the dilator 5 is extracted from its channel or passage 14 (compare FIGS. 6 and 7 with FIG. 5). The introducer 6 is then ready to allow for introduction of the electrode 1 in a manner as shown in FIGS. 7 and 8, i.e., a first section 1a of the implanted electrode extends into the vein 2 beyond the first end portion 6a of the introducer 6 and a second section 1b of the electrode 1 extends beyond the exposed and accessible second end portion 6b of the introducer. The direction of insertion of the pacemaker electrode 1 is indicated by the arrow Pf4 which is shown in FIG. 7. The introducer 6 has fulfilled its primary purpose as soon as the tip 1c of the fully inserted electrode 1 reaches its destination, e.g., the heart of the patient.

Figure 10:
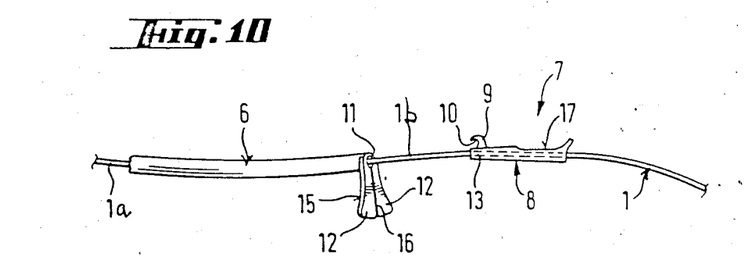
FIG. 10 shows the structure of FIG. 9, with the flat edge faces of the two handgrip portions in abutment with one another so that the handgrip portions form a handle which can be manipulated by hand to facilitate extraction of the first end portion of the introducer from the vein and severing of the introducer in the course of and subsequent to the extracting step by a severing device having a single knife.
Figure 11:
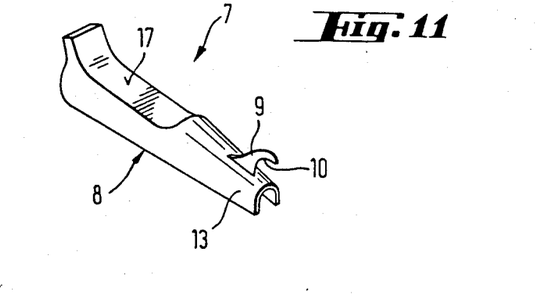
FIG. 11 is an enlarged perspective view of the improved severing device.
Figure 12:
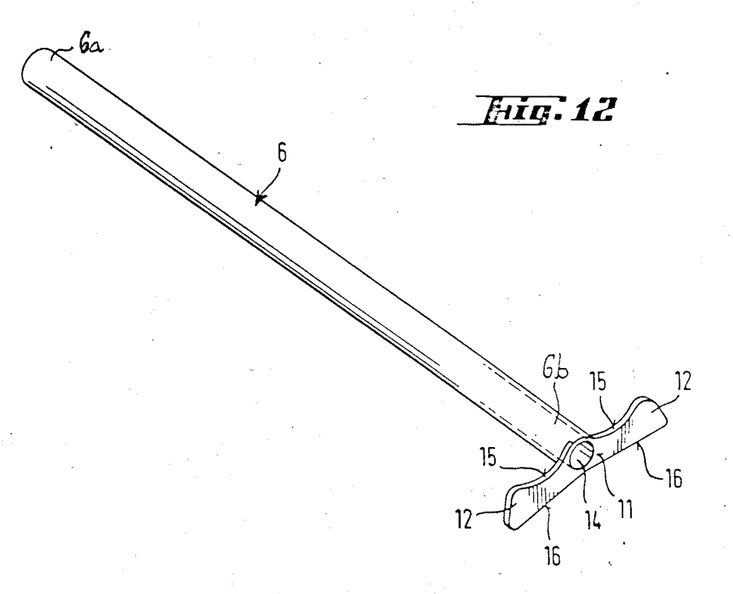
FIG. 12 is an enlarged perspective view of the introducer.
Figure 13:
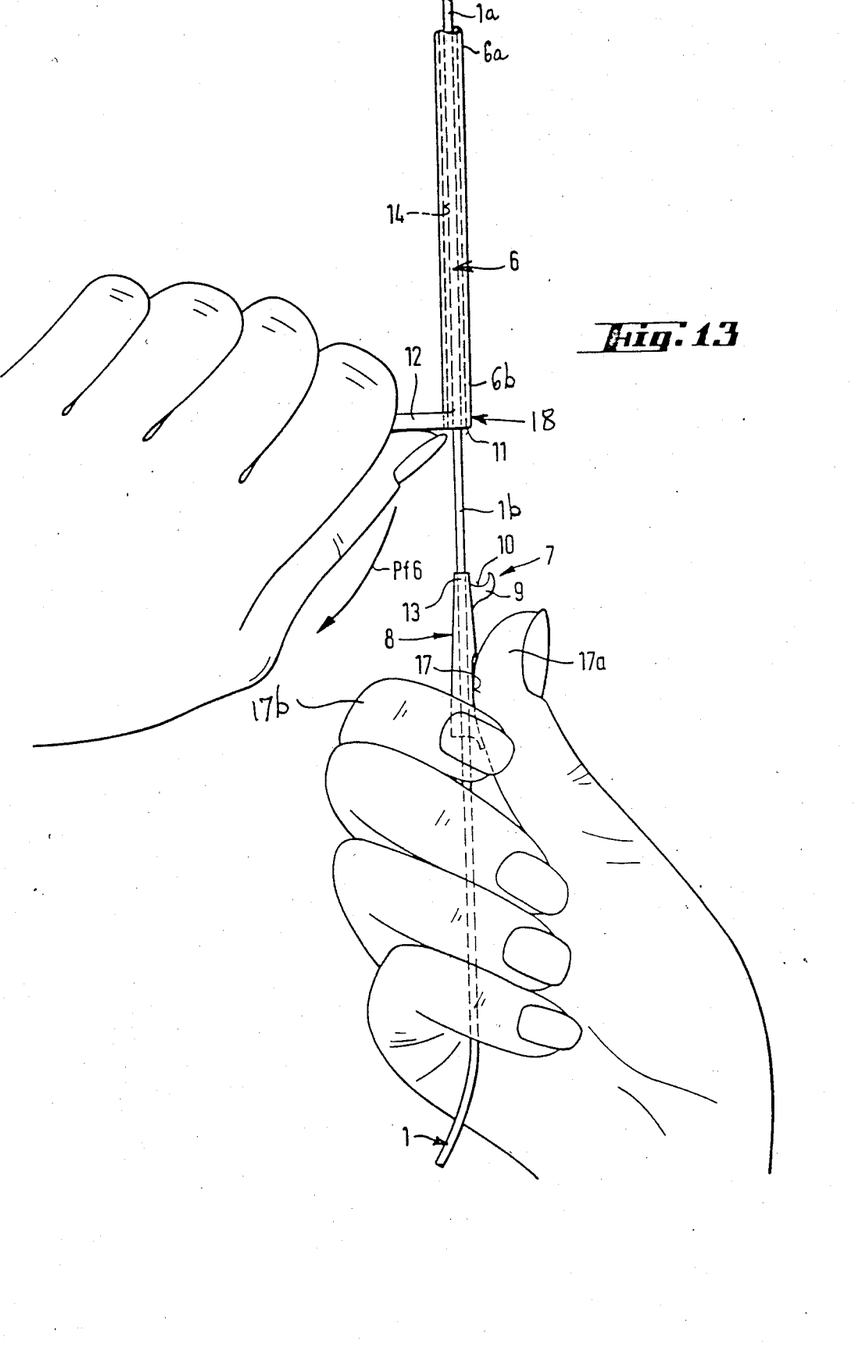
FIG. 13 is an enlarged elevational view of the apparatus, showing the introducer in the process of moving toward and against the cutting edge of the knife which forms part of the severing device.

The introducer 6 must be withdrawn from the vein 2 and must be separated from the electrode 1 as soon as the latter is properly anchored in the body of the patient, i.e., as soon as the tip 1c reaches its destination. Extraction of the introducer 6 from the vein 2 would be simple but for the fact that the rear end of the section 1b of the electrode 1 carries a customary plug (reference may be had, for example, to FIG. 7 of the aforementioned U.S. Pat. No. 4,345,606) whose diameter exceeds the diameter of the passage 14 in the introducer 6 so that the latter cannot be slipped over the plug. Consequently, it is necessary to sever the introducer 6 in order to allow for its separation from the section 1b of the electrode 1. The plug at the rear end of the section 1b is necessary to connect the electrode with the pacemaker, such as the one disclosed in the aforementioned U.S. Pat. No. 4,345,606. Another solution would be that of severing the plug from the electrode section 1b or of attaching the plug to the section 1b subsequent to removal of the introducer 6. Neither of these solutions has been found to be practical and, therefore, the apparatus comprises a novel and improved severing device 7 which is shown in FIGS. 10, 11 and 13 and serves to slit the introducer 6 open from the end portion 6b to the end portion 6a in the course of and following the extraction of the end portion 6a from the body of the patient. As can be best seen in FIG. 12, the introducer 6 is a sleeve which is circumferentially complete from the end portion 6a to the end portion 6b, i.e., the sleeve is not formed with a slit or with one or more longitudinally extending weakened portions prior to insertion of the end portion 6a into the vein. However, the material (preferably a synthetic plastic substance) of the introducer 6 can be severed by the cutting edge 10 of a knife 9 which forms part of the severing device 7 and is integral with or securely attached to an elongated trough-shaped supporting portion or holder 8 of the device 7.

As can be seen in FIG. 11, the supporting portion 8 of the severing-device 7 has a substantially U-shaped cross-sectional outline (it is also possible to use a supporting portion which has a substantially C-shaped cross-sectional outline). In other words the supporting portion 8 resembles an elongated trough which preferably extends longitudinally beyond both sides of the knife 9, as considered in the longitudinal direction of the exposed second section 1b of the implanted electrode 1. This facilitates proper gripping of the supporting portion 8 by the fingers (e.g., by the thumb 17a and index finger 17b) of the person who is in charge of extracting the introducer 6 from the body of the patient and of simultaneously severing the introducer so that it can be separated from the electrode section 1b in the space between the locus where the electrode 1 extends into the vein and the locus of the aforediscussed plug. The knife 9 extends substantially radially from the supporting portion 8 and its cutting edge 10 faces the exposed end face 11 of the second end portion 6b of the introducer 6 when the latter assumes the position of FIG. 10 (in which the end portion 6a still extends into the vein, not shown) and the supporting portion 8 surrounds and frictionally engages the section 1b of the implanted electrode 1. A supporting portion 8 having a substantially U-shaped cross-sectional outline prior to deformation of its preferably elastic material (e.g., a synthetic plastic substance) can be converted into a supporting portion with a substantially C-shaped cross-sectional outline when the supporting portion is properly grasped by the fingers 17a and 17b in a manner as shown in FIG. 13. The length of the supporting portion 8 is preferably selected with a view to allow for convenient and reliable grasping by one hand of the person who is in charge of extracting the introducer 6 from the vein 2 and of severing the introducer so that it can be separated from the section 1b of the pacemaker electrode 1.

Figure 9:
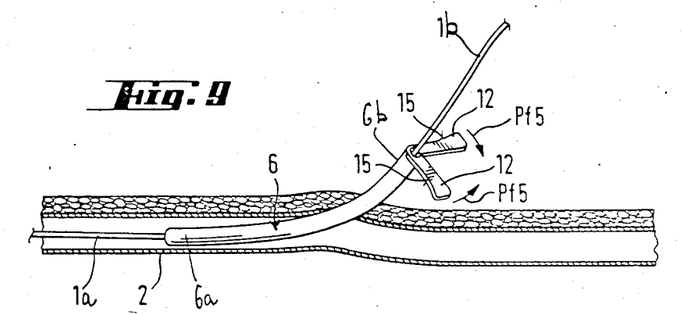
FIG. 9 shows the structure of FIG. 8 with the handgrip portions at the exposed end of the introducer moved partly toward each other.

The end portion 6b of the introducer 6 carries two wing-like handgrip portions 12 which normally extend radially of the introducer and are located diametrically opposite each other. In the illustrated embodiment, the handgrip portions 12 are integral parts of the introducer 6 and each thereof has a flat or substantially flat edge face 16 as well as a second edge face which is provided with a recess 15 in the form of a relatively shallow flute. At least one of the handgrip portions 12 can be moved close to the other handgrip portion so that the flat edge faces 16 are close to or actually contact each other (see FIG. 10) whereby the two handgrip portions form a relatively large handle which can be grasped by two fingers of one hand (see FIG. 13) while the fingers 17a, 17b of the other hand grasp the supporting portion 8 of the severing device 7. FIG. 9 shows that each of the two handgrip portions 12 is movable about the axis of the introducer 6 toward the other handgrip portion (note the arrows Pf5) until the two handgrip portions reach the positions which are shown in FIG. 10, i.e., until such handgrip portions form the aforediscussed handle. Such movement of the handgrip portions 12 from the positions of FIG. 8, through the positions of FIG. 9 and to the positions of FIG. 10 results in at least some stretching or tensioning of the material of the introducer 6 at the location 18 (i.e., diametrically opposite the handle including the two abutting handgrip portions) which facilitates initial severing of the introducer 6 by the cutting edge 10 of the knife 9 when the handle including the handgrip portions 12 is pulled in the direction which is indicated in FIG. 13 by the arrow Pf6, namely in a direction having a component in the axial direction of the section 1b of the electrode 1 and a component at right angles to the axis of the section 1b. Once the cutting edge 10 has severed the end portion 6b (i.e., once the cutting edge 10 has penetrated into the end face 11 at the location 18), the severing of successive intermediate portions and ultimately of the end portion 6a of the introducer 6 can be completed in response to the exertion of a relatively small force. In other words, the person in charge of removing the introducer 6 simply continues to grasp the handle including the abutting handgrip portions 12 and continues to move such handle along the arcuate path which is denoted by the arrow Pf6.

FIGS. 10, 11 and 13 show that the supporting portion 8 of the severing device 7 has a substantially conical terminal or tip 13 which can be received in and then at least partially seals the exposed end of the passage 14 in the introducer 6 to thus prevent any or to prevent pronounced outflow of blood via introducer 6 while the latter is being extracted from the vein and while it is in the process of being slotted longitudinally by the cutting edge 10 of the knife 9. The terminal 13 need not be exactly or pronouncedly conical, as long as it can sealingly engage the end face 11 or as long as it can enter into and sealingly engage the internal surface of the end portion 6b of the introducer 6. The terminal 13 is preferably close or immediately adjacent to the cutting edge 10 of the knife 9 so that severing of the introducer 6 can begin practically immediately in response to entry of the terminal 13 into the end portion 6b. The supporting portion 8 of the severing device 7 can be caused to surround the section 1b of the electrode 1 in close or immediate proximity of the end portion 6b prior to start of extraction of the end portion 6a from the vein so that severing of the introducer 6 begins substantially simultaneously with the start of extraction of the end portion 6a. This is desirable and advantageous because it contributes to a shortening of the interval which is required to extract the end portion 6a from the body of the patient and to separate the introducer 6 from the section 1b of the pacemaker electrode 1. The terminal 13 further ensures that the end portion 6b of the introducer 6 is reliably guided toward and against the cutting edge 10 during the initial stage of extraction of the end portion 6a from the body, i.e., after the terminal 13 has penetrated into the oncoming end of the passage 14 in the introducer 6. This even more reliably ensures that the cutting edge 10 can sever the end portion 6b at the desired location (18).

The purpose of flutes 15 in the respective edge faces of the handgrip portions 12 at the end face 11 of the end portion 6b of the introducer 6 is to allow for more predictable engagement by two fingers which are used to move the handgrip portions 12 along the arcuate paths indicated by the arrows Pf5 before the thus formed handle is gripped in a manner as shown in FIG. 13 and pulled in the direction which is indicated by the arrow Pf6 of FIG. 13.

The material of the supporting portion 8 of the severing device 7 is preferably an elastomeric substance so that the supporting portion can be deformed whereby its internal surface can engage the external surface of the section 1b of the electrode 1 in order to reduce the likelihood of slippage of the supporting portion relative to the electrode while the cutting edge 10 of the knife 9 severs the introducer 6. That part of the supporting portion 8 which extends rearwardly and beyond the knife 9 (i.e., in a direction away from the end portion 6b as viewed in FIG. 13) is preferably formed with one or more recesses in the form of shallow flutes 17 to allow for more convenient and more reliable engagement by the fingers (such as the thumb 17a) of the person in charge of extracting and separating the introducer 6. The fingers 17a and 17b can be used to shift the entire severing device 7 toward the end face 11 of the end portion 6b before the person in charge begins to extract the end portion 6a from the body of the patient. The flute 17 can be replaced with serrations at the exterior of the supporting portion 8, or such serrations can be provided in addition to one or more flutes 17.

An important advantage of the severing device 7 is that it can be used to sever or slit open a reasonably stiff but severable introducer so that the latter can properly guide the electrode 1 during implantation in a manner as shown in FIGS. 7, 8 and 9 without excessive bending, buckling and/or other deformation which could prevent rapid and predictable implantation of the electrode.

An important advantage of the improved severing device is that the apparatus can utilize a relatively simple, relatively rugged and relatively rigid introducer which need not be slotted prior to use and which need not be provided with longitudinally extending perforations, external grooves or otherwise weakened portions which are used in conventional introducers to allow for predictable slitting during or subsequent to extraction from the body of the patient. This is accomplished by the expedient of providing the improved severing device which can be readily applied around the exposed section of a properly implanted electrode or an analogous slender elongated object. The cutting edge of the knife cannot damage the insulating layer which is provided at the exterior of the electrode because the knife never contacts any part of the electrode, either during or subsequent to implantation. The insulation on the electrode is much more likely to be damaged or destroyed if the introducer is to be severed by shears or by a similar implement in order to allow for its separation from the implanted electrode without removing the aforediscussed plug.

The introducer can be made of a single piece of suitable severable material, i.e., it is not necessary to employ two slotted tubes which are telescoped into each other in a manner such that they can be separated from the exposed section of an implanted electrode which already carries a plug for connection to the pacemaker. Composite introducers are bulky and expensive. On the other hand, an introducer which is slotted prior to introduction into the body of a patient is unduly weakened and is likely to buckle during implantation of an electrode. The same applies for introducers which are weakened by external grooves or by one or more rows of perforations. Moreover, a slotted or perforated introducer is likely to permit the escape of substantial quantities of body fluid during implantation of an electrode and during subsequent detachment of the introducer from the implanted object. The introducer which is used in the apparatus can be designed with a view to ensure that its characteristics (such as rigidity, suppleness, flexibility, sealing action at the point of penetration into the body, inner and outer diameters and/or others) are selected exclusively with a view to ensure predictable and rapid implantation of the electrode and not primarily or largely with a view to allow for separation from the implanted electrode without the need to remove the plug.

The improved severing device exhibits the important advantage that it can be rapidly applied to and engaged with as well as rapidly separated from the exposed section of the implanted electrode and is highly unlikely to damage or otherwise adversely affect the insulation on or any other part of the electrode. The length of the supporting portion and the configuration of its flute or flutes can be readily selected in such a way that the supporting portion reliably maintains the knife in an optimum position for severing of the introducer and that it can be conveniently and predictably grasped by the fingers of one hand to hold it against slippage in the longitudinal direction of the exposed section of the implanted electrode. The material of the supporting portion can be elastic but nevertheless sufficiently rigid to hold the knife in an optimum orientation to ensure predictable severing of the portion 6b, of the intermediate portions and finally of the end portion 6a of the introducer in response to exertion of a pull in the direction of arrow Pf6 as described in connection with FIG. 13. At such time, the handgrip portions perform several important functions, namely of forming a satisfactory handle and also of enabling one hand of the person in charge to exert a pull in the direction of arrow Pf6 and to thus ensure that the severing action of the cutting edge begins at the location 18, i.e., diametrically opposite the handle.

The provision of a severing device whose supporting portion is made of or contains elastomeric material which comes into contact with the exposed section of the implanted electrode is desirable and advantageous because such elastomeric material is highly unlikely to damage or destroy the insulation on the electrode, and such material also ensures that the supporting portion can frictionally engage the exposed section of the electrode so as to ensure that the severing device can be held at an optimum distance from the point of penetration of the electrode into the body of the patient without any slippage along the section 1b. Moreover, the forces which the fingers 17a and 17b apply to the exposed section 1b of the implanted electrode 1 are distributed (at least substantially uniformly) all the way between the two longitudinal ends of the elastic supporting portion 8 so that the latter is even less likely to damage the insulation of the electrode.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A device for slitting open a tubular introducer serving to facilitate insertion of a pacemaker electrode, a catheter or an analogous elongated slender object into the body of a patient and having an exposed end portion from which the object extends, said device comprising an elongated manually deformable elastic supporting portion having a first end, a second end and a longitudinally extending slot between said ends so that it can be slipped sideways onto the object to at least partially surround the object adjacent the exposed end portion of the introducer and to facilitate the deformation of said supporting portion; and a knife provided on said supporting portion and having a cutting edge facing one of said ends to face the end portion of the introducer when the supporting portion at least partially surrounds the object so that the introducer can be severed by moving it relative to the object against the cutting edge while the supporting portion is deformed by hand between said knife and the other of said ends and is thereby maintained in frictional engagement with the object.

2. The device of claim 1, wherein said supporting portion extends beyond said knife in at least one direction as considered longitudinally of the object.

3. The device of claim 1, wherein said supporting portion has a substantially U-shaped cross-sectional outline.

4. The device of claim 1, wherein said supporting portion has a substantially C-shaped cross-sectional outline.

5. The device of claim 1, wherein said supporting portion comprises an elastomeric material.

6. The device of claim 1, wherein said supporting portion is recessed to conform to at least one finger of a hand which is used to hold said supporting portion in engagement with the object.

7. The device of claim 6, wherein said recessed supporting portion has a flute and said knife is located between such flute and said one end, the object.

8. The device of claim 1, wherein said one end of said supporting portion incudes a terminal which is receivable in the end portion of the introducer to at least partially step the outflow of body fluids by way of the introducer while the introducer extends into the body.

9. The device of claim 8, wherein said terminal is a substantially conical tip of said supporting portion.

10. The device of claim 8, wherein said cutting edge is adjacent to said terminal.

* * * * *